United States Patent [19]

Shields

[11] Patent Number: 5,241,178
[45] Date of Patent: Aug. 31, 1993

[54] INFRARED GRAIN ANALYZER WITH CONTROLLABLE MEASUREMENT WAVELENGTH

[76] Inventor: John Shields, Thorpton Demesne, Thorpton, Morpeth, Northumberland, England

[21] Appl. No.: 742,052

[22] Filed: Aug. 6, 1991

Related U.S. Application Data

[63] Continuation of Ser. No. 679,994, Mar. 29, 1991, abandoned, which is a continuation of Ser. No. 493,998, Mar. 15, 1990, abandoned.

[30] Foreign Application Priority Data

Mar. 16, 1989 [GB] United Kingdom ............... 8906020

[51] Int. Cl.⁵ ...................... G01N 21/35; G01N 21/47
[52] U.S. Cl. .................................. 250/339; 250/341; 250/360.1
[58] Field of Search ............ 250/339, 341, 343, 358.1, 250/359.1, 360.1, 574, 576, 573; 356/445, 446, 448, 418, 244

[56] References Cited

U.S. PATENT DOCUMENTS

| | | | |
|---|---|---|---|
| 4,037,970 | 7/1977 | Webster et al. | 356/418 |
| 4,176,916 | 12/1979 | Carpenter | 356/418 |
| 4,421,411 | 12/1983 | Ida | 356/418 |
| 4,422,760 | 12/1983 | Webster | 356/244 |
| 4,466,076 | 8/1984 | Rosenthal | 356/418 |
| 4,538,908 | 9/1985 | Webster | 250/576 |
| 4,662,755 | 5/1987 | Aoki | 356/414 |
| 4,806,764 | 2/1989 | Satake | 250/339 |

OTHER PUBLICATIONS

Roche et al., "Tilt Tunable Ultra Narrow-Band Filters For High Resolution Infrared Photometry" *Applied Optics* vol. 14, No. 3, Mar., 1975 pp. 765–770.

Primary Examiner—Constantine Hannaher
Assistant Examiner—Jim Beyer
Attorney, Agent, or Firm—Barnes, Kisselle, Raisch, Choate, Whittemore & Hulbert

[57] ABSTRACT

Apparatus for quantitative analysis of a material sample, such as whole grain, as a function of optical characteristics thereof includes a light source and a solid state detector of silicon or other suitable construction. A material sample is positioned between the light source and the detector, and light energy is focused through the sample onto the detector at a plurality of preselected wavelengths in the near-infrared range of 800–1100 nm. Illumination wavelength is selectively controlled by an opaque disc having a central axis and a plurality of apertures around the periphery at uniform radius from the disc axis. A plurality of filter elements are carried by the disc over respective ones of the peripheral apertures and have transmission characteristics corresponding to the plurality of preselected wavelengths. The filter elements are carried in a continuous circumferential array around the disc periphery, with the array including at least one opaque section for chopping light energy incident on the detector. The disc is rotated about its axis in a continuous motion so that each filter element in turn intersects light energy transmitted through the sample. Analysis electronics is responsive to light energy incident on the detector at the plurality of preselected wavelengths to indicate a preselected characteristic of the material sample.

5 Claims, 4 Drawing Sheets

INFRARED GRAIN ANALYZER WITH CONTROLLABLE MEASUREMENT WAVELENGTH

This is a continuation of copending application Ser. No. 07/679,994 filed on Mar. 29, 1991 now abandoned, which is a continuation of copending application Ser. No. 07/493,998 filed on Mar. 15, 1990 now abandoned.

The present invention is directed to electrophotometric quantitative analysis of a material sample, and more specifically to apparatus for measuring concentration of a constituent such as moisture, oil, protein and starch in a food product such as whole grain.

BACKGROUND AND OBJECTS OF THE INVENTION

It has heretofore been proposed to measure concentrations of water, oil (fat), protein and/or starch (carbohydrates) in food products, such as dairy, meat, fruit and grain products, using infrared and near-infrared quantitative analysis techniques. "An Introduction to Near-Infrared Quantitative Analysis," presented by R. D. Rosenthal at the 1977 Annual Meeting of the American Association of Cereal Chemists, surveys the basic technology in which infrared energy is directed onto a material sample at a number of different wavelengths selected as a function of absorption characteristics of the material constituents of interest, and constituent concentrations are obtained as a function of energy transmitted through or reflected by the sample at the various selected wavelengths. In one device illustrated in the Rosenthal paper, a number of optical filter elements are carried by a flat disc positioned between a light source and the sample. The disc is incrementally rotated to bring each filter in turn into alignment between the light source and the sample, and a detector is positioned on the opposite side of the sample to measure energy transmitted through the sample. The optical data readings are processed employing conventional multiple linear regression analysis techniques to obtain concentration readings of the various constituents. U.S. Pat. Nos. 4,415,809 and 4,447,725 disclose apparatus for measuring concentrations of moisture, fat, protein and lactose in dairy products See also U.S. Pat. Nos. 4,193,116, 4,253,766 and 4,627,008.

In apparatus of the subject character heretofore proposed, thermal-type optical detectors have generally been employed. Operating characteristics of detectors of this type require that energy to be measured be incident thereon for a substantial time, on the order of one-half second, for the thermal properties to stabilize and thereby permit reliable measurements to be obtained. Where the art has proposed use of detectors having more rapid optical response characteristics, the artisan has continued to employ previous illumination techniques. Consequently, substantial time is required to obtain a measurement at each preselected measurement wavelength.

Another problem characteristic of the art lies in limitations imposed on the number of available measurement wavelengths. That is, the number of available wavelengths has generally been limited by size of the filter-holding disk, which in turn is limited by available space. A change in desired wavelengths requires a physical change of filters, a time-consuming and exacting operation, particularly where the filter must be "tuned" to desired wavelength.

It is therefore a general object of the present invention to provide apparatus for quantitative analysis of material samples, such as whole grains, that is of compact and economical construction, that is sufficiently versatile as to be employed in conjunction with a number of differing test materials, such as differing cereal grains, that does not require sample preparation, that includes capability for performing measurements at a substantial number of selectable wavelengths over the chosen near-infrared range, and that provides rapid material analysis with minimum operator intervention and without sacrifice of measurement accuracy.

SUMMARY OF THE INVENTION

In accordance with the present invention, apparatus for quantitative analysis of a material sample, such as whole grain, as a function of optical characteristics thereof includes a light source and a solid state detector of silicon or other suitable construction. A material sample is positioned between the light source and the detector, and light energy is focused through the sample onto the detector at a plurality of preselected discrete infrared wavelengths, preferably in the near-infrared range of 800-1100 nm. Analysis electronics is responsive to light energy incident on the detector at the plurality of preselected wavelengths to indicate a preselected characteristic of the material sample - e.g., concentration of one or more sample constituents. In accordance with one distinguishing feature of the present invention, illumination wavelength is selectively controlled by an opaque disc having a central axis and a plurality of apertures around the periphery at uniform radius from the disc axis. A plurality of filter elements are carried by the disc over respective ones of the peripheral apertures and have transmission characteristics corresponding to the plurality of preselected wavelengths. The disc is rotated about its axis in a continuous motion, rather than an intermittent motion as in the prior art, so that each filter element in turn intersects light energy transmitted through the sample. In the preferred embodiment of the invention, the filter elements are carried in a continuous circumferential array around the disc periphery, with the array including at least one opaque section for chopping light energy incident on the detector.

Preferably, apparatus in accordance with the invention further includes facility for selectively and variably controlling wavelength of radiation transmitted onto the detector through each of the filter elements. In one embodiment of the invention, this function is accomplished by tilting the filter disc axis of rotation in a direction orthogonal thereto so as to vary angle of incidence of the illumination beam onto each of the filter elements, and thereby vary wavelength of energy transmitted through the filter elements onto the sample and detector. In another embodiment of the invention, a wavelength control or tuning disc is positioned between the light source and the filter disc. The tuning disc has a plurality of apertures around the periphery thereof at differing radii with respect to the axis of the illumination beam. The tuning disc is selectively rotated such that its periphery intersects light energy prior to incidence onto the filters, with angle of such incidence varying as a function of the effective radius of the apertures in the tuning disc at that portion of the tuning disc periphery that intersects the light. Thus, with either embodiment, a number of wavelength readings greatly exceeding the number of filter elements can be obtained for enhanced measurement capabilities e.g., accuracy and resolution.

The optical detector preferably comprises an array of silicon detectors having a response time on the order of a few nanoseconds. The light source preferably comprises a tungsten-halogen lamp having a quartz envelope. As applied specifically to analysis of whole grains, the test samples preferably are positioned in the light path, between the filter disc and the detector array, using a vertically oriented sample chute and a shutter or trap at the lower end of the chute for holding samples in position during a measurement cycle. Grain samples are selectively fed to or from the chute using a controlled vibrator coupled to a sample tray.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
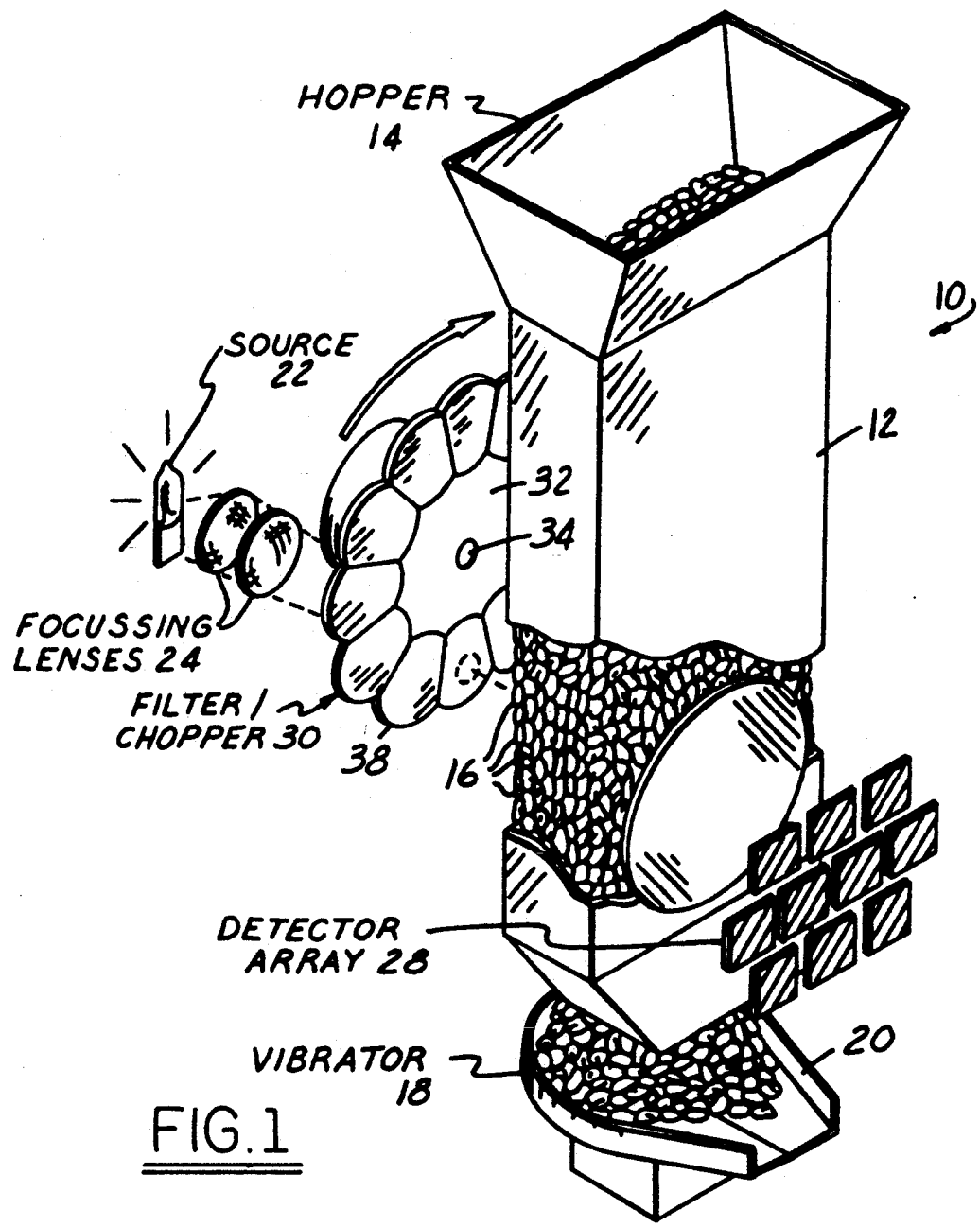
FIG. 1 is a perspective schematic diagram of apparatus for quantitative analysis of whole grain samples in accordance with one presently preferred embodiment of the invention.

FIG. 1 illustrates apparatus 10 in accordance with one presently preferred embodiment of the invention for quantitative analysis of constituent concentrations in whole grain test samples. Apparatus 10 includes a vertical chute 12 having a flared hopper 14 at the upper end thereof for receiving test samples of grain 16 to be analyzed. The lower end of hopper 12 tapers to an outlet end above a vibrator assembly 18 that includes a tray 20 positioned beneath the chute. Radiation from a light source 22 such as a tungsten-halogen lamp with quartz envelope, producing good energy characteristic in the region 800 to 1100 RM, is directed through focusing lenses 24 and through transparent sidewalls of hopper 12 onto an array 28 of solid state optical detectors, such as silicon array detectors.

Figure 2:
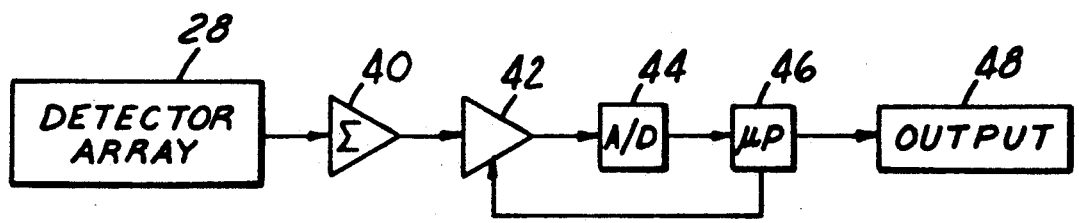
FIG. 2 is a functional block diagram of apparatus electronics in the analyzer of FIG. 1.

A filter/chopper assembly 30 (FIGS. 1 and 6) is positioned between focusing lenses 24 and sample chute 12. Filter/chopper assembly 30 comprises a flat opaque disc 32 coupled to the output shaft 34 of a drive motor 36 for rotating disc 32 about its central axis. The periphery of disc 32 includes a circumferential array of apertures. A plurality of wedge-shaped filter elements 38 are carried in a continuous circumferential array about the periphery of disc 32 over respective ones of the apertures, with the exception of a single opaque segment for chopping light energy incident through the grain sample onto the detector array and thereby acting as a position reference. Filter/chopper assembly 30 is positioned relative to focusing lenses 24 so that filters 38 sequentially intersect light energy passing from source 22 through the sample contained in hopper 12 onto detector array 28, and thereby transmit through the sample onto the detector infrared energy at a preselected narrow wavelength band corresponding to optical characteristics of the respective filter elements. Preferably, the axis of disc 32 is positioned with reference to the illumination light path so that the light beam intersects each filter substantially centrally of the filter, as shown in FIG. 1. In the embodiment of FIG. 1, the disc axis is at fixed angle to the illumination path, preferably parallel thereto As shown in FIG. 2, the several elements of detector array 28 are summed and connected through an amplifier 40. The output of amplifier 40 is connected through a calibration amplifier 42 and an analog-to-digital convertor 44 to the data input of a microprocessor 46. Gain and offset of amplifier 42 are controlled by microprocessor 46. Microprocessor 46 has a data output coupled to suitable output display devices 48, such as a digital display, a printer or the like, for indicating constituent concentrations in the measurement test samples.

Figure 3:
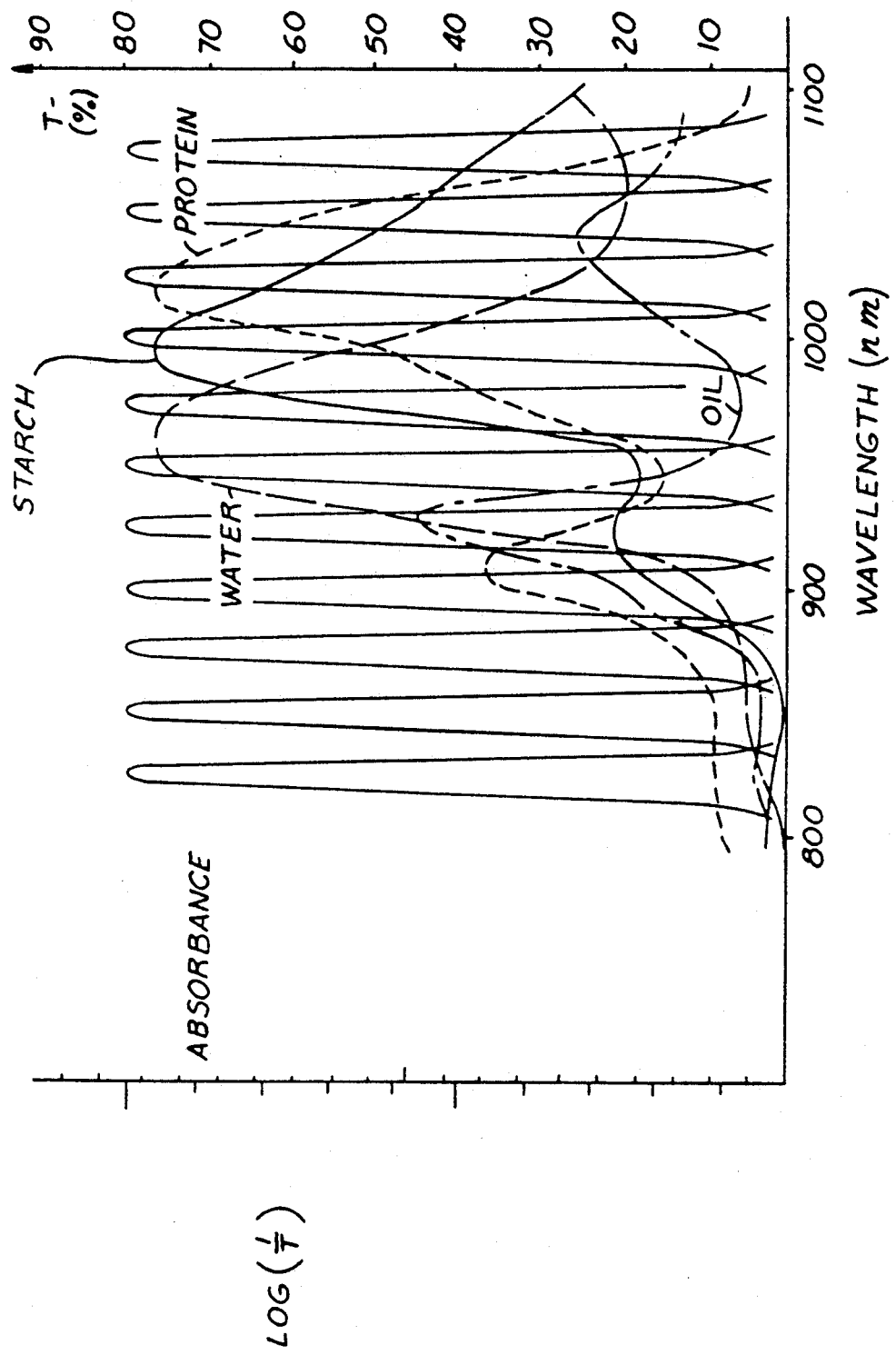
FIG. 3 is a graphic illustration useful in explaining operation of the invention.

In operation, vibrator 18 is first activated to dump a sample held in tray 20, and thereby to permit flow of grain through the superimposed hopper 12 so as to bring a fresh test sample to the measurement light path. As filter/chopper assembly is rotated in a continuous motion, the summed output of detector array 28 is sampled at successive signal peaks, corresponding to successive peak transmissions at the wavelengths of filters 38 in turn. The measurement signals so obtained are then employed using multivariate statistical methods for obtaining concentration readings of the various sample constituents FIG. 3 illustrates absorptivity spectra (log 1/T) of water, protein, starch and oil constituents of whole grains in the near infrared range of 800–1100 nanometers. Superimposed on the absorptivity spectra are the transmission characteristics (% T) $38a$–$38k$ of the eleven filters 38 carried by disc 32, with the twelfth filter position being occupied by an opaque chopping reference as previously described. Filters 38 preferably have half bandwidths on the order of 15 nm.

Figure 4:
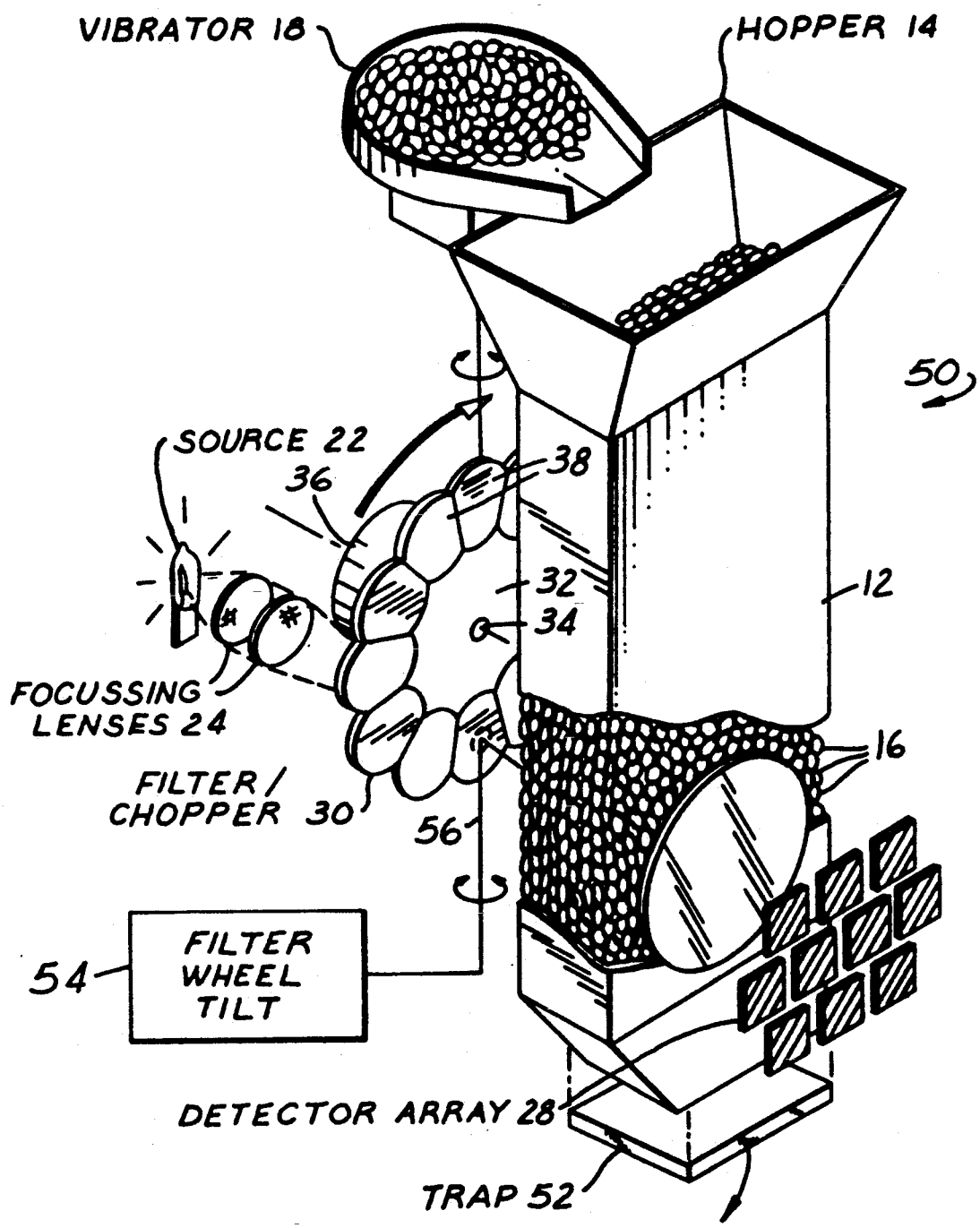
FIGS. 4 and 5 are perspective schematic diagrams of respective modified embodiments of the invention.

FIG. 4 illustrates a grain analyzer 50 in accordance with a modified embodiment of the invention, and in which elements identical to those hereinabove discussed in connection with FIGS. 1–3 are indicated by correspondingly identical reference numerals. In apparatus 50, vibrator 18 is positioned at the upper end of hopper 14 above chute 12, and the lower end of chute 12 is selectively opened or closed by a trap 52 coupled to a suitable control device (not shown) Filter/chopper assembly 30 is coupled to a device 54 for selectively tilting the filter/chopper assembly about an axis 56 orthogonal to the axis of rotation of filter disc 32 - i.e., about a vertical axis 56 in the orientation of FIG. 4. In this way, angle of incidence of light energy from source 22 and focusing lenses 24 is selectively varied by tilting the filter/chopper assembly, and the wavelength transmission characteristics of each filter element is correspondingly variably controlled.

For example, a first series of eleven measurement readings may be taken with filter disc 32 in neutral position at which the axis of rotation is parallel to the light path through the filter elements. The filter disc may then be tilted a few degrees (in the orientation of FIG. 4) and a second series of eleven measurement readings obtained, this time at wavelengths that differ slightly from the first series of measurement wavelengths. The filter/chopper assembly may then be tilted further from the neutral position, and a third series of measurement readings obtained, again at wavelengths different from those of the first and second series. Thus, in accordance with this important feature of the embodiment in FIG. 4, any number of multiple series of measurement readings may be obtained at differing measurement wavelengths to enhance accuracy and resolution of the measurement apparatus.

Figure 5:
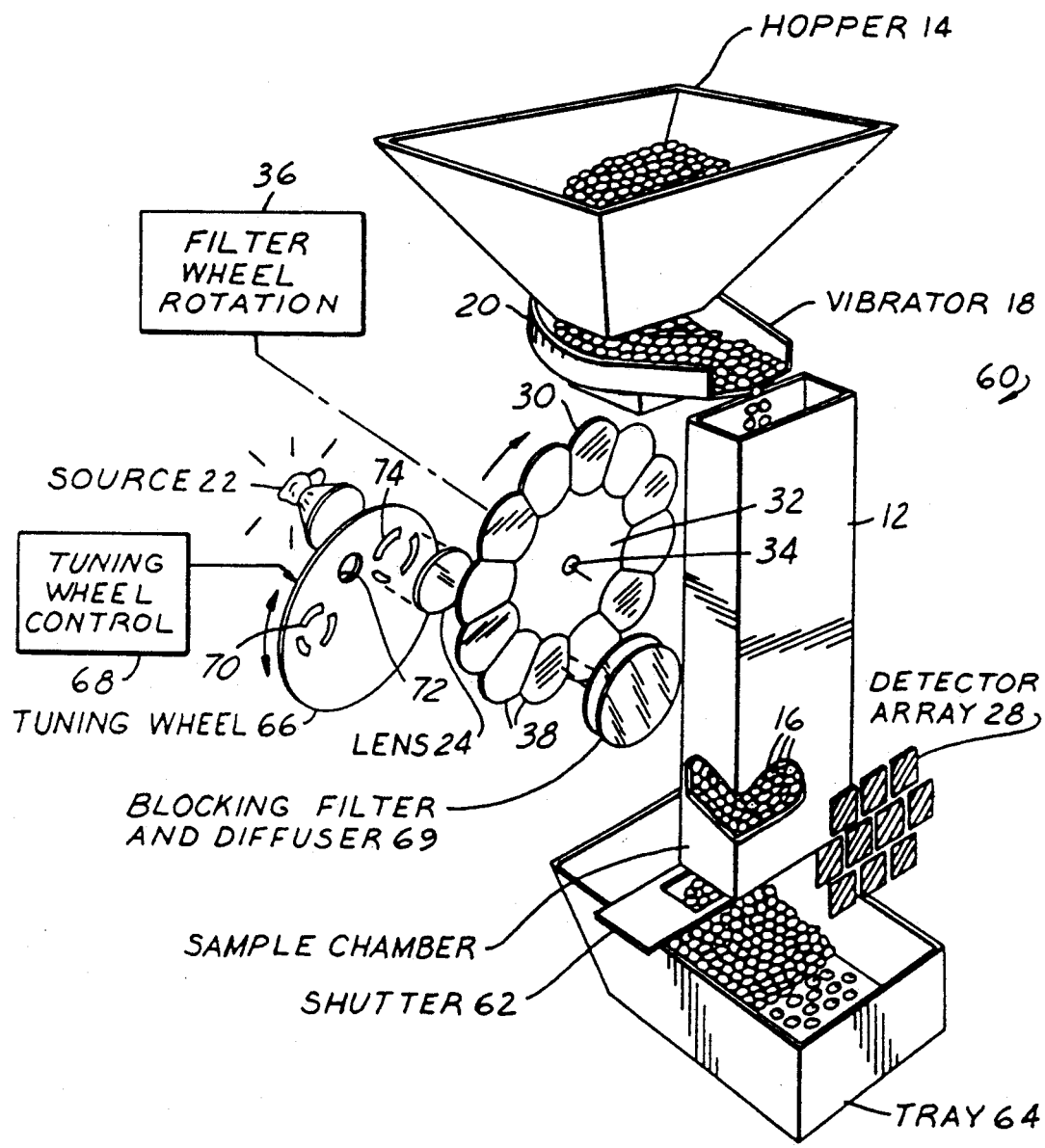

FIG. 5 illustrates apparatus 60 in accordance with a third embodiment of the invention in which vibrator 18 is positioned between hopper 14 and the upper end of chute 12. The lower end of chute 12 is coupled to a shutter 62 for selectively dumping the content of chute 12 into a sample tray 64. Filter/chopper assembly 30 is again coupled to a drive motor 36 for continuous rotation in the clockwise direction. A tuning wheel or disc 66 is positioned between source 22 and filter/chopper assembly 30, and is coupled to a suitable control 68 for selectively varying angle of incidence of light energy onto each of the filter elements 38. Tuning wheel 66 includes a series of three apertures 70, 72, 74 at differing effective radii with respect to the axis of the illumination beam. Middle aperture 72 takes the form of a circular opening coaxial with the axis of light energy transmitted by source 22 onto filter assembly 30. Aperture 70 takes the form of three concentric kidney-shaped passages at a first diameter with respect to the axis of illumination light energy, and aperture 74 takes the form of three kidney-shaped passages at a second greater diameter with respect to the axis of illumination energy. A blocking filter and diffuser arrangement 69 is positioned between assembly 30 and sample chute 12.

Thus, light energy transmitted through aperture 72 is orthogonal to the plane of filter elements 38. Light energy incident on the filter elements through aperture 70, however, will be at a slight angle with respect to such orthogonal direction, whereas light energy transmitted through aperture 74 will be at a greater angle with reference to such orthogonal direction. Thus, by selectively positioning apertures 70, 72, 74 to intersect the illumination light beam, three series of eleven measurement readings—i.e., up to thirty-three measurement readings—can be obtained at different measurement wavelengths while employing only eleven filters elements 38.

I claim:

1. Apparatus for quantitative analysis of a granular material sample as a function of infrared absorption characteristics thereof comprising:

a light source for radiating energy in the near-infrared range of about 800 to 1100 nm, a silicon detector array, means for positioning a granular material sample between said source and said detector array such that a portion of said light energy incident on the sample from said source is transmitted through and scattered by the granular sample onto said detector array, means responsive to light energy incident on said detector array from said source through the sample to indicate a preselected characteristic of the granular material sample in said positioning means, and means for focusing light energy from said source through the granular material sample in said positioning means onto said detector array at a plurality of discrete preselected near-infrared wavelengths comprising an opaque disc having a central axis and a plurality of apertures in the periphery thereof at uniform radius from said axis, a plurality of individual filter elements carried by said disc over said apertures and having transmission characteristics corresponding to said plurality of discrete preselected wavelength, said array of filter elements including at least one opaque section for chopping light energy incident on said detector array to synchronize operation of said means responsive to light energy to rotation of said disc, means for rotating said disc about said axis in a continuous rotation such that each said filter element in turn intersects light energy transmitted through the sample onto the detector, and means for selectively and variably controlling wavelength of radiation transmitted onto said detector array through each said filter element during continuous rotation of said disc without interrupting rotation of said disc such that light energy transmitted through each said filter element generates a plurality of said discrete preselected near-infrared wavelength at said detector array on successive rotations of said disc, said means for selectively and variably controlling wavelength of transmittal onto said detector array through each said filter element comprising means for selectively varying angle of incidence of light energy onto said filter means including tuning means positioned between said source and said filter means and having a plurality of apertures at differing radii with respect to the axis of illumination from said source to said filter means, and means for controllably positioning said tuning means such that a selected one of said apertures intersects said light energy.

2. The apparatus set forth in claim 1 wherein said tuning means comprises a disc having said apertures at the periphery thereof.

3. The apparatus set forth in claim 1 wherein said source comprises a tungsten-halogen lamp having a quartz envelope.

4. The apparatus set forth in claim 1 for analyzing samples of whole grain wherein said sample-positioning means comprises a vertically oriented sample chute and means for selectively holding a sample in said chute.

5. The apparatus set forth in claim 4 wherein said sample-positioning means further comprises a vibrator for selectively feeding grain samples through said chute.

* * * * *